United States Patent [19]
Kretzers

[11] Patent Number: 5,997,563
[45] Date of Patent: Dec. 7, 1999

[54] IMPLANTABLE STENT HAVING VARIABLE DIAMETER

[75] Inventor: Leo J. G. Kretzers, VK Sittard, Netherlands

[73] Assignee: Medtronic, Inc., Minneapolis, Minn.

[21] Appl. No.: 09/161,236

[22] Filed: Sep. 28, 1998

[51] Int. Cl.⁶ .................................................. A61M 29/00
[52] U.S. Cl. ................................ 606/198; 623/1; 623/12
[58] Field of Search ........................... 606/1, 108, 194, 606/198, 200; 623/1, 12

[56] References Cited

U.S. PATENT DOCUMENTS

| | | |
|---|---|---|
| 5,470,313 | 11/1995 | Crocker et al. . |
| 5,476,508 | 12/1995 | Amstrup . |
| 5,545,210 | 8/1996 | Hess et al. . |
| 5,697,971 | 12/1997 | Fischell et al. . |
| 5,725,549 | 3/1998 | Lam ............................................. 623/1 |
| 5,797,951 | 8/1998 | Mueller ................................... 606/198 |

*Primary Examiner*—Michael Buiz
*Assistant Examiner*—William Lewis
*Attorney, Agent, or Firm*—Thomas F. Woods; Harold Patton; Michael J. Jaro

[57] ABSTRACT

A stent which minimizes or solves the problem of restenosis. The present stent is designed so as to have a cyclical change in diameter, the change in diameter corresponding to the changes in blood pressure caused by the cardiac cycle. The present stent is constructed through several structural members, each structural member interlocking in a fashion which permits the stent diameter to be altered from a first, diastolic diameter to a second, systolic diameter. This variable diameter is provided through a series of joints between the interlocking structural members. The joints may be provided in any acceptable manner, including an interlocking dog bone configuration, an interlocking elastic coupling, mating struts, as well as interlocking guides.

35 Claims, 4 Drawing Sheets

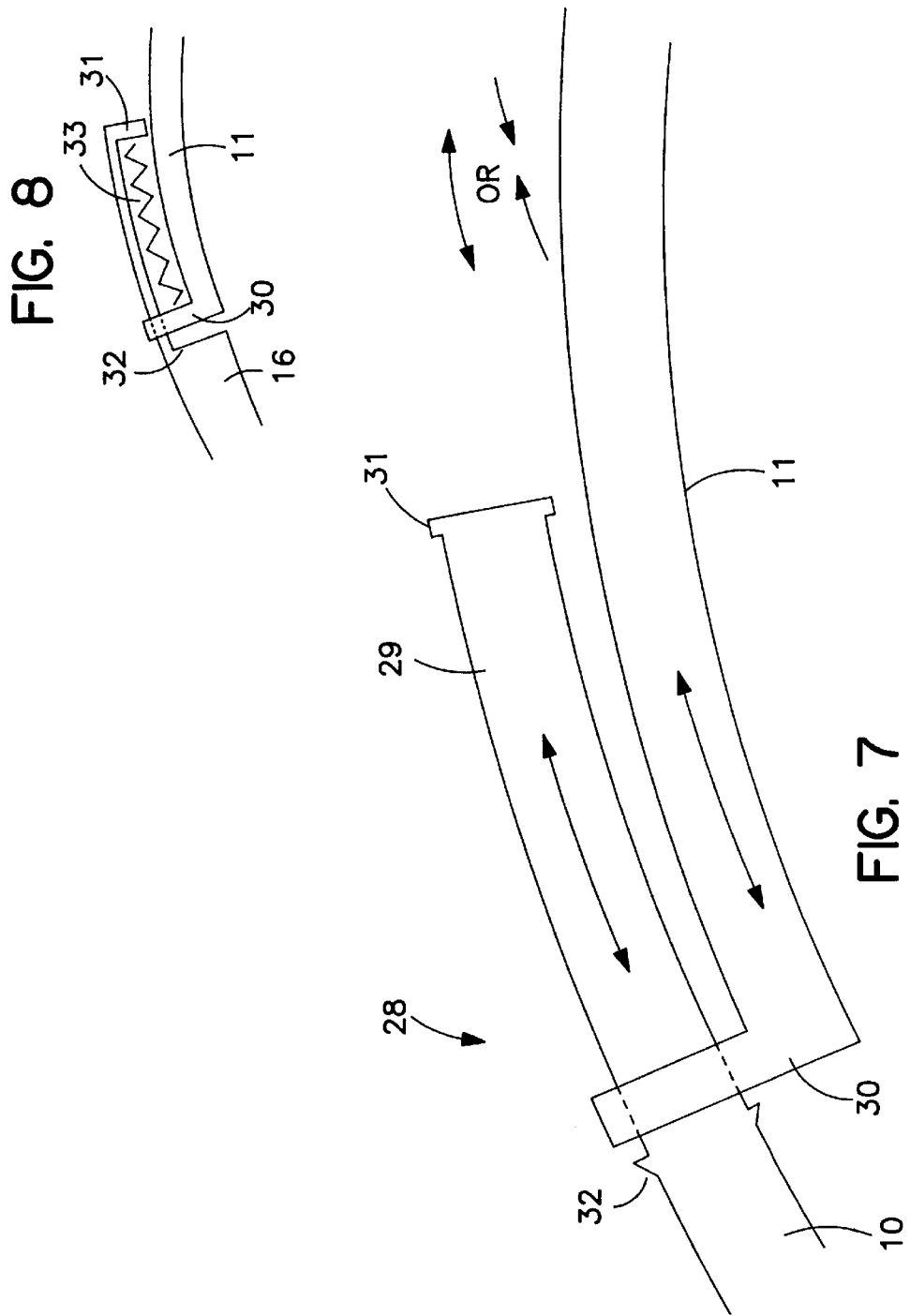

IMPLANTABLE STENT HAVING VARIABLE DIAMETER

FIELD OF THE INVENTION

The present invention relates to an implantable medical device and, particularly, an enhanced stent which, more physiologically, conforms and adjusts to the arterial wall.

BACKGROUND OF THE INVENTION

Among the most important medical devices developed in the last half of the century is that of the implantable stent. Such a stent is used to maintain the patency or passageway through an artery or vein. Stents have found their greatest use in the heart propping open cardiac arteries.

Although stents have provided a major advancement in therapy for patients suffering from cardiac diseases, they still, nonetheless, fail to perform in all cases and for all time. Among the problems stented patients face is that of restenosis. Restenosis refers to the accumulation and subsequent arterial blockage in an artery near the stent. That is, although the stent provides an immediate improvement in blood flow, the artery in the region of the stent again occludes leaving the patient in the same predicament as he was prior to the stent's implantation.

Thus, among the objects of the present invention is to provide a stent which will minimize or eliminate the problem of restenosis.

SUMMARY OF THE INVENTION

The present invention provides a stent which minimizes or solves the problem of restenosis. The present stent is based on the observed physiology of arteries and veins. Namely, arteries and veins increase and decrease in their diameters corresponding to the increase and decrease of blood pressure, i.e. as the heart beats the blood pressure and blood vessel diameter changes. The present stent is designed so as to have a cyclical change in diameter, the change in diameter corresponding to the changes in blood pressure caused by the cardiac cycle. The present stent is constructed through several structural members, each structural member interlocking in a fashion which permits the stent diameter to be altered from a first, diastolic diameter to a second, systolic diameter. This variable diameter is provided through a series of joints between the interlocking structural members. The joints may be provided in any acceptable manner, including an interlocking dog bone configuration, an interlocking elastic coupling, mating struts, as well as interlocking guides.

BRIEF DESCRIPTION OF THE DRAWINGS

FIG. 7 depicts a further alternative joint used in the present invention.

FIG. 8 depicts a further alternative joint used in the present invention.

The Figures are not necessarily to scale.

DETAILED DESCRIPTION OF THE DRAWINGS

As described above, the present invention is directed to solving the problem of restenosis in blood vessels which have a stent implanted thereon. The inventor believes a necessary and, perhaps, sufficient basis for this restenosis is due to the rigidity of past stent designs. Namely, past stent designs have been implanted in a manner in which their diameter designs do not vary once implanted into a blood vessel. The physiology of a blood vessel, however, is such that the blood vessel diameter is constantly varying. With each beat of the heart the blood pressure in the body changes or oscillates between a higher blood pressure (so-called systolic pressure) to a lower pressure (so-called diastolic pressure). The diameter of all blood vessels also correspond with changes in this blood pressure cycle. Past stent designs, however, have had a fixed diameter once implanted, such that the blood vessel in the region of the stent would no longer oscillate with the normal blood pressure cycle. The inventor believes this inability of the stent and, thus, the blood vessel wall to oscillate with the normal blood pressure cycle is physiologically abnormal and serves as a basis for the problem of restenosis.

The present invention solves this problem by providing a stent which features a series of elastic joints which permit the stent to couple to the arterial wall without inhibiting the arterial wall from moving in a physiological manner with the blood pressure cycle.

Figure 1:
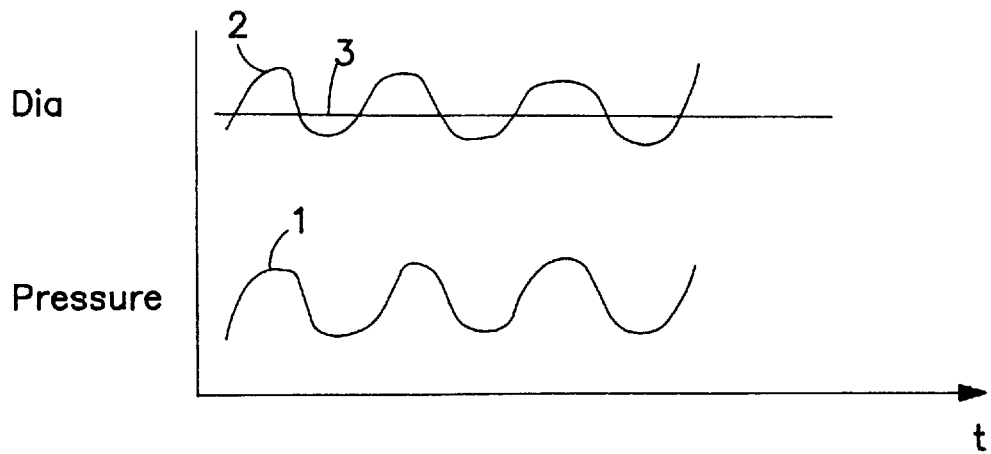
FIG. 1 depicts the blood pressure cycle and corresponding blood vessel diameter cycle for both a stented and unstented blood vessel.

FIG. 1 depicts the blood pressure cycle and corresponding blood vessel diameter cycle for both a stented and unstented blood vessel. As seen, in a healthy patient, the blood pressure oscillates between a high value and a low value. This oscillation is caused by the beating of the heart. In a normal patient the blood vessel diameter and corresponding changes is seen here as line 2. When a blood vessel has a stent implanted, however, the stent has typically been expanded, at least, until or even beyond the previous largest physiological diameter of the blood vessel, depicted here as line 3. Because the blood vessel is no longer undergoing changes corresponding to the blood pressure, the inventor believes a restenosis response is caused in many patients, often leading again to the occlusion of the blood vessel. The present invention prevents this re-occlusion by providing a stent which provides a variable diameter such that the blood vessel implanted continues to undergo a cyclic blood vessel diameter.

Figure 2:
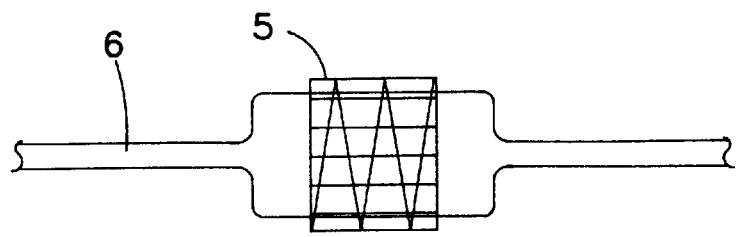
FIG. 2 depicts a stent, according to the present invention, on a balloon delivery device.

FIG. 2 depicts a stent, according to the present invention, on a balloon delivery device. As seen, stent 5 may be mounted on to a balloon delivery device as is well known in the art. That is the balloon is mounted upon the end of an angioplasty catheter. Through such a balloon delivery device the stent may be percutaneously introduced and implanted into the blood vessel as is well known in the art.

Figure 3:
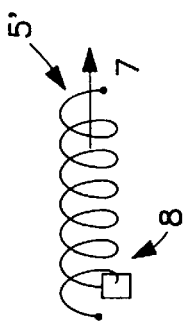
FIG. 3 depicts a stent according to the present invention.

FIG. 3 depicts a stent according to the present invention. As seen, stent 5 is fashioned as an interlocking series of structural members which provide a cylindrical lumen 7 therethrough. Although a particular design of interlocking members is shown in FIG. 3, it should be noted the particular form of the interlocking members is not essential to the present invention, but rather the elastic joints 8 which provide the ability for the interlocking members to be elasticity deformed and permit the member to have a cyclical diameter variation are considered essential. Although not perhaps entirely clear from this view, each structural member and its associated components which provide the joint are curved such that the resultant stent is cylindrical.

Figure 4:
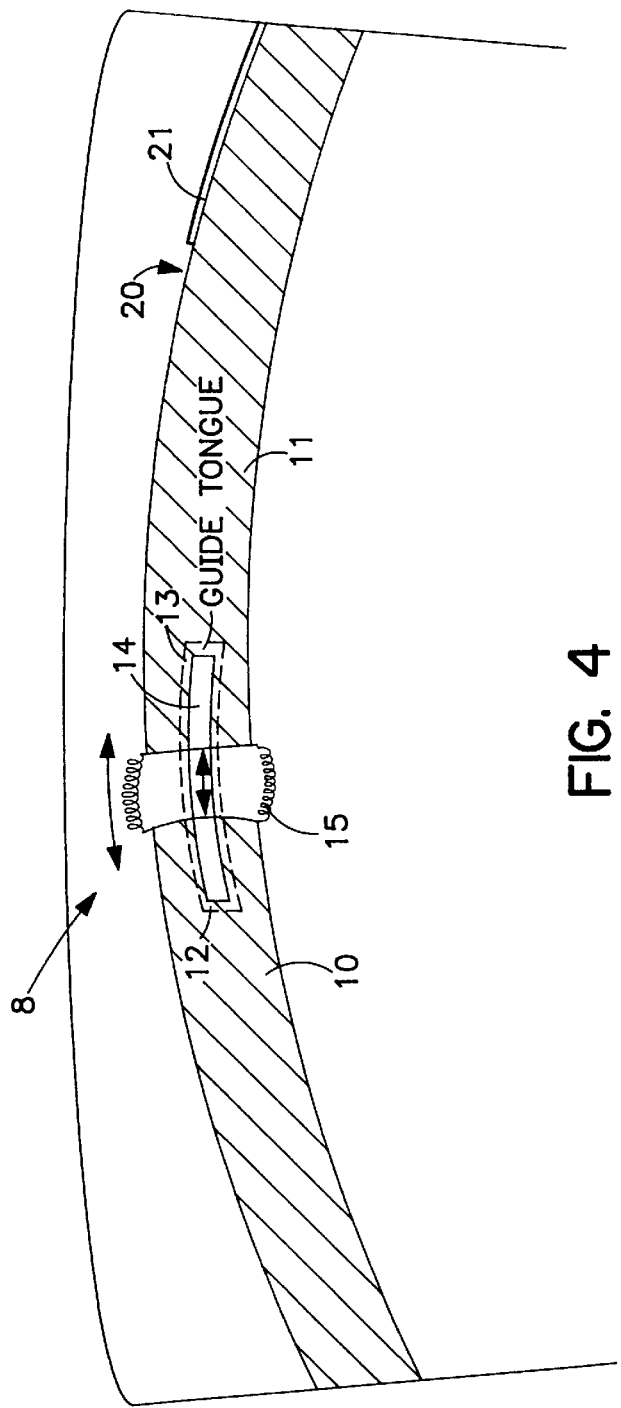
FIG. 4 depicts a joint used in the stent of the present invention.

FIG. 4 depicts a joint used in the stent of the present invention. As seen, joint 8 is provided between a first structural member 10 and a second structural member 11 used in the stent. Each structural member has a corresponding guide slot 12 and 13 between which a guide tongue 14 is provided. Guide tongue and slots ensure the structural members maintain alignment. Further coupling the structural members is an elastic coupling element 15. Elastic coupling element provides an elastic joint between the structural members such that they may move away from and towards one another within the specified range of movement without undergoing plastic deformation. Thus, the joint provides an elastic movement between the two members which, ultimately, permits the stent to have an elasticity variable diameter. Elastic coupling element may be provided through either one or more structures as shown in the present figure, or through a one-piece or multi-piece polymer element made of an acceptable elastomer. Elastomeric element may take the form of a ring fixed to each of the shown structural elements.

Ultimately, the present invention, thus, permits a stent which would have a sufficient number of illustrated joints to achieve elastic coupling with the arterial wall such that the movement of the arterial wall forces the stent to undergo smaller changes in its diameter.

In a alternative embodiment, the outer surface 20 of the structural elements may be further coated 21 so as to enhance embodiment of the stent into or with the arterial wall. Coating may take the form of a collagen, at least particularly fixed using any of the well know fixation techniques, epoxy for example, deposited on the outer diameter surface of the stent. Collagen preferably should be at least particularly fixed using any of the well know fixation techniques, including that shown in the co-pending U.S. patent application Ser. No. 08/912,778 of Hendriks et al. entitled Process For Making A Bioprosthetic Device filed on Aug. 18, 1997 for example and incorporated herein by reference. It should be noted, however, other coatings may also be applied, alone or in combination with the collagen.

Figure 5:
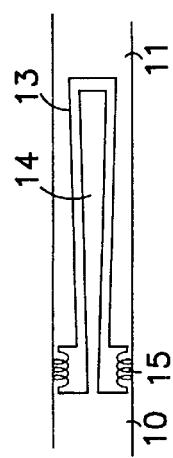
FIG. 5 depicts an alternative joint used in the present invention.

FIG. 5 depicts an alternative joint used in the present invention. In this embodiment structural element 10 features guide tongue 14 which mates into guide slot 13 in the corresponding structural element 11. It should be noted, tongue 14, in this embodiment, preferably is curved to correspond with the cylindrical shape of the stent All other elements and features of this design are similar otherwise to those shown in FIG. 4.

Figure 6:
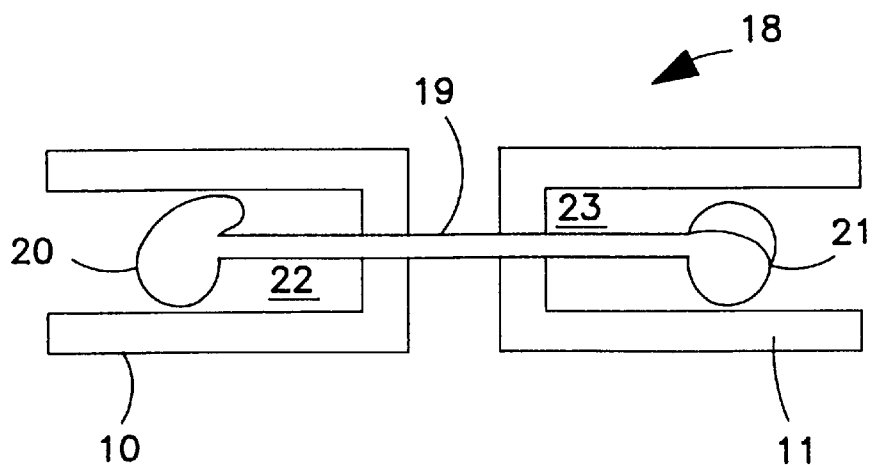
FIG. 6 depicts a further alternative joint used in the stent according to the present invention.

FIG. 6 depicts a further alternative joint used in the stent according to the present invention. In this embodiment an interlocking dog bone expansion joint 8 is provided to generally permit the stent to be moved from a first diameter to a second diameter and thereafter to the first diameter. Joint 18 is provided by the interlocking of the first structural element 10 to the second structural element 11 by dog bone 19. As seen, dog bone features, on opposite ends, larger diameter stops 20 and 21. Each stop is provided within a larger lumen 22 and 23 in the structural element respectively. As further seen, end caps of each structural element thereafter stops dog bone from moving outside corresponding structural element.

FIG. 7 depicts a further alternative joint used in the present invention. As seen, joint 28 is provided through a particular interlocking between first structural member 10 and second structural member 11. In particular, a rail guide joint is provided through a rail portion 29 of first structural element 10 and a corresponding guide element 30 on a second structural element 11. Rail portion 29 runs between stops 31 and 32 provided on first structural element 10. Through this design the structural elements may be moved with respect to one another between two pre-determined joints such that the ultimate diameter of the stent may be varied.

FIG. 8 depicts a further alternative joint used in the present invention. As seen, FIG. 8 joint corresponds to that shown in FIG. 7 but for the additional provision of a spring element 33 between first and second structural elements 10 and 11. In particular, spring is positioned between stop 31 and guide 30. Spring, thus, provides a general outward bias to the stent diameter. Due to the minor force of the spring, however, the vessel wall may generally be able to maintain the stent in a less than maximum diameter except when the corresponding higher blood pressure portions of the cycle are experienced. Of course, in an alternative embodiment spring, thus, provides a generally inward bias to the stent diameter.

Figure 9:
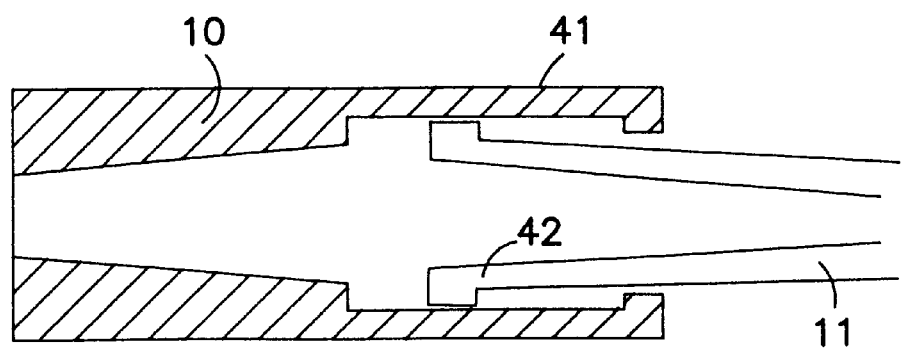
FIG. 9 depicts a further alternative joint used in the present invention.

FIG. 9 depicts a further alternative joint used in the present invention. As seen, first and second structural elements 10 and 11 meet together through a series of mating struts or interlocking overlaps 41 and 42. It should be appreciated, however, that the interlocking overlaps are particularly designed such that the stent may have a much lower diameter prior to implant due to the hollow feature of one or more of the structural elements. This is illustrated in FIG. 10, shown below.

Figure 10:
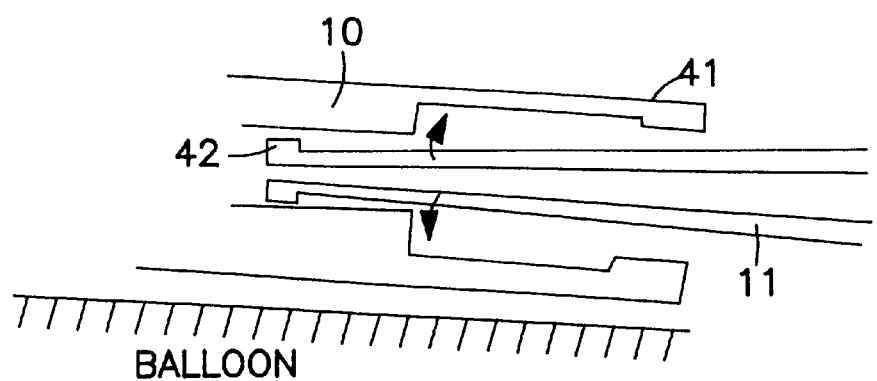
FIG. 10 shows the embodiment shown in FIG. 9 prior to implant

FIG. 10 shows the embodiment shown in FIG. 9 prior to implant in which the interlocking overlaps have been collapsed into one another to permit the stent to achieve its smallest diameter. As can be appreciated, when the interlocking overlaps are nestled or mated together in this fashion, the stent achieves a similar diameter. After implant, the stent is expanded such that the overlaps interlock between two predetermined points. The mating struts or interlocking overlaps are designed such that their natural position is separated and thus not like that shown in FIG. 10 but rather like that in FIG. 9, thus when the stent diameter is expanded using the balloon, the struts pop out and interlock as shown It should be further noted, from this embodiment, that the joint provided is non-elastic such that the structural elements may move relative to one another without being biased in any one direction. As discussed above, such a non-elastic and non-plastically deformable stent joint is provided so that the arterial wall can open and close the stent diameter corresponding to the normal physiologic response to the arterial wall to blood pressure cycle.

In a still further embodiment the elastic joint may be made temporarily rigid such that the stent may be introduced and expanded by conventional plastic deformation techniques and yet thereafter the joint or joints may be available to permit the stent to freely conform to the variable blood vessel diameter. In the particular alternative embodiment the joints are temporarily immobilized using a bioabsorbable material Mannitol. Of course, many other compounds may also be used to achieve the function of making the stent joints temporarily rigid such that the stent may be introduced and expanded by conventional plastic deformation techniques and yet thereafter the joint or joints may be available to permit the stent to freely conform to the variable blood vessel diameter.

Although a specific embodiment and alternative embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

I claim:

1. A stent comprising a first structural member;

a second structural member; and joint means linking the first and second members together, the joint means for reversibly permitting the stent to expand from a first diameter to a second diameter and thereafter back to the first diameter.

2. The stent according to claim 1 further comprising the joint means having means for engaging with a blood vessel wall and permitting the stent to expand from a first diameter to a second diameter and thereafter back to the first diameter by forces transmitted from the blood vessel wall.

3. The stent according to claim 1 wherein the joint means comprise a guide slot in the first structural member and a corresponding guide tongue in the second structural member.

4. The stent according to claim 3 further comprising an elastic spring element disposed between the first and second structural members.

5. The stent according to claim 4 wherein first structural member is curved.

6. The stent according to claim 5 wherein the guide tongue is curved.

7. The stent according to claim 1 wherein first structural member has a first guide slot and second structural member has a second guide slot.

8. The stent according to claim 7 further comprising a guide tongue, the guide tongue positioned at least partially within the first guide slot.

9. The stent according to claim 1 wherein coupling the first structural member and second structural member is an elastic coupling element.

10. The stent according to claim 9 wherein the elastic coupling element provides a bias between the first structural member and second structural member.

11. The stent according to claim 10 wherein the bias causes the first structural member and second structural member to move away from one another.

12. The stent according to claim 10 wherein the bias causes the first structural member and second structural member to move towards one another.

13. The stent according to claim 1 wherein an outer surface of the first structural element is coated with means for promoting embodiment of the stent into the arterial wall.

14. The stent according to claim 13 wherein the coating is collagen.

15. The stent according to claim 1 wherein the joint means comprises a dog bone element disposed to interlock with the first structural element and the second structural element whereby the joint means may be moved to permit the stent to be moved from a first diameter to a second diameter and thereafter to the first diameter.

16. The stent according to claim 15 wherein the dog bone element has a first end diameter, a middle diameter and a second end diameter, the first end diameter and the second end diameter larger than the middle diameter, each stop positioned within a larger lumen in the first and second structural elements respectively.

17. The stent according to claim 1 wherein the joint means comprises a rail guide joint, the rail guide joint provided through a rail portion on the first structural element and a corresponding guide element on the second structural element 11.

18. The stent according to claim 17 further comprising a spring element positioned between the first and the second structural element.

19. The stent according to claim 1 wherein the joint means comprises a series of interlocking overlaps disposed on the first structural element and the second structural element.

20. The stent according to claim 1 further comprising means for temporarily immobilizing the joint means.

21. The stent according to claim 20 wherein means for temporarily immobilizing the joint means comprises a bioabsorbable material.

22. A stent and delivery balloon system comprising a delivery balloon mounted upon an angioplasty catheter;

a stent, the stent comprising a curved first structural member mounted upon the delivery balloon;

a curved second structural member mounted upon the delivery balloon; and joint means linking the first and second members together, the joint means for reversibly permitting the stent to expand from a first diameter to a second diameter and thereafter back to the first diameter, the joint means mounted upon the delivery balloon.

23. The stent and delivery balloon system according to claim 22 further comprising the joint means having means for engaging with a blood vessel wall and permitting the stent to expand from a first diameter to a second diameter and thereafter back to the first diameter by forces transmitted from the blood vessel wall.

24. The stent and delivery balloon system according to claim 22 wherein the joint means comprise a guide slot in the first structural member and a corresponding guide tongue in the second structural member.

25. The stent and delivery balloon system according to claim 24 further comprising an elastic spring element disposed between the first and second structural members.

26. The stent and delivery balloon system according to claim 25 wherein the elastic spring element provides a bias between the first structural member and second structural member.

27. The stent and delivery balloon system according to claim 26 wherein the bias causes the first structural member and second structural member-to move away from one another.

28. The stent and delivery balloon system according to claim 26 wherein the bias causes the first structural member and second structural member to move towards one another.

29. The stent and delivery balloon system according to claim 22 wherein an outer surface of the first structural element is coated with means for promoting embodiment of the stent into the arterial wall.

30. The stent and delivery balloon system according to claim 29 wherein the coating Is collagen.

31. The stent and delivery balloon system according to claim 22 wherein the joint means comprises a dog bone element disposed to interlock with the first structural element and the second structural element whereby the joint means may be moved to permit the stent to be moved from a first diameter to a second diameter and thereafter to the first diameter.

32. The stent and delivery balloon system according to claim 22 wherein the joint means comprises a rail guide joint, the rail guide joint provided through a rail portion on the first structural element and a corresponding guide element on the second structural element.

33. The stent and delivery balloon system according to claim 22 wherein the joint means comprises a series of interlocking overlaps disposed on the first structural element and the second structural element.

34. The stent and delivery balloon system according to claim 22 further comprising means for temporarily immobilizing the joint means.

35. The stent and delivery balloon system according to claim 34 wherein means for temporarily immobilizing the joint means comprises a bioabsorbable material.

* * * * *